United States Patent [19]

Hall

[11] Patent Number: 4,459,405

[45] Date of Patent: Jul. 10, 1984

[54] DESACETYLCEPHALOSPORIN SULFONES

[75] Inventor: David A. Hall, Indianapolis, Ind.

[73] Assignee: Eli Lilly and Company, Indianapolis, Ind.

[21] Appl. No.: 442,076

[22] Filed: Nov. 16, 1982

[51] Int. Cl.$^3$ ............................................ C07D 501/26
[52] U.S. Cl. ................................ 544/28; 260/239 A; 544/30; 544/90; 548/218
[58] Field of Search ..................................... 544/28, 30

[56] References Cited

U.S. PATENT DOCUMENTS 3,597,421  8/1971  Webber ................................ 260/243
4,399,131  8/1983  Durckheimer et al. .............. 544/28

OTHER PUBLICATIONS

W. Durckheimer et al., in G. I. Gregory, Ed., *Royal Society of Chemistry, Special Publication No. 38–Recent Advances in the Chemistry of β–Lactam Antibiotics*, London, Chapter 4, pp. 46–51, (1981).

*Primary Examiner*—Paul M. Coughlan, Jr.
*Attorney, Agent, or Firm*—Paul C. Steinhardt; Arthur R. Whale

[57] ABSTRACT 7-(S)-Acylamino-3-hydroxymethyl-3-cephem sulfones are disclosed. These compounds are intermediates in the synthesis of 1-oxa β-lactam antibiotics.

19 Claims, No Drawings

DESACETYLCEPHALOSPORIN SULFONES

SUMMARY OF THE INVENTION

This invention relates to cephalosporin compounds. In particular it relates to 7-(S)-acylamino-3-hydroxymethyl-3-cephem-4-carboxylic acid sulfones and the salts and the esters thereof, which are useful intermediates in the preparation of 1-oxa β-lactam antibiotics.

DETAILED DESCRIPTION

This invention relates to 7-(S)-acylamino-3-hydroxymethyl cephem sulfones represented by the formula 1

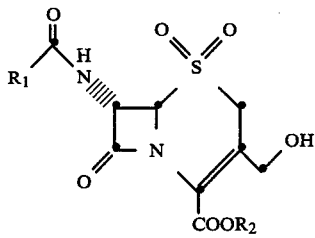

wherein $R_1$ is
a. $C_1$ to $C_7$ alkyl, $C_3$ to $C_7$ alkenyl, chloromethyl, dichloromethyl, 4-carboxybutyl, 4-formylbutyl, 4-protected carboxybutyl, 4-amino-4-carboxybutyl or 4-protected amino-4-protected carboxybutyl;
b. $C_1$ to $C_6$ alkoxy, $C_3$ to $C_6$ cycloalkyloxy, benzyloxy or substituted benzyloxy, wherein the substituents are one to three groups chosen from the group consisting of $C_1$ to $C_4$ alkyl, $C_1$ to $C_4$ alkoxy and chloro;
c. 1,4-cyclohexadienyl, phenyl or substituted phenyl wherein the substituents are one or two groups chosen from the group consisting of chlorine, bromine, hydroxy, trifluoromethyl, $C_1$ to $C_4$ alkyl, $C_1$ to $C_4$ alkoxy, carboxy, carboxymethyl, hydroxymethyl, aminomethyl and protected aminomethyl;
d. an arylalkyl group of the formula
  $R'—(O)_m—CH_2—$
  wherein $R'$ is 1,4-cyclohexadienyl, phenyl or substituted phenyl wherein the substituents are one or two groups chosen from the group consisting of chlorine, bromine, hydroxy, trifluoromethyl, $C_1$ to $C_4$ alkyl, $C_1$ to $C_4$ alkoxy, carboxy, carboxymethyl, hydroxymethyl, aminomethyl and protected aminomethyl, and m is zero or one;
e. a substituted arylalkyl group of the formula

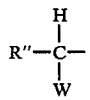

wherein $R''$ is $R'$ as defined above, 2-thienyl, or 3-thienyl; W is hydroxy, carboxy or protected carboxy, amino or protected amino;
f. a heteroarylmethyl group of the formula $R'''—CH_2—$ wherein $R'''$ is 2-thienyl, 3-thienyl, 2-furyl, 3-furyl, 2-thiazolyl, 5-tetrazolyl or 1-tetrazolyl; and $R_2$ is hydrogen, a carboxylic acid protecting group, lithium cation, sodium cation, or potassium cation.

The compounds of this invention are prepared by contacting a 7-(S)-acylamino-3-acetoxymethyl cephem sulfone ("3-acetoxymethyl compound") compound of the formula 2

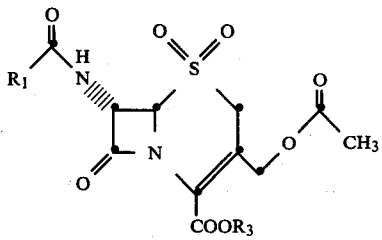

in an aqueous solution buffered from about pH 6 to about pH 8 with the enzyme citrus acetylesterase, immobilized on silica gel. In the formula 2 $R_1$ is an acyl group as defined above, and $R_3$ is hydrogen, lithium cation, potassium cation or sodium cation.

As used in the above general description of the 7-(S)-acylamino-3-hydroxymethyl cephem sulfone compounds and the corresponding 7-(S)-acyl-3-acetoxymethyl cephem sulfone starting material, the term "$C_1$ to $C_7$ alkyl" refers to methyl, ethyl, n-propyl, n-butyl, isobutyl, pentyl, n-hexyl, n-heptyl, cyclohexyl, and like aliphatic hydrocarbon chains. "$C_3$ to $C_7$ alkenyl" refers to the unsaturated hydrocarbon chains such as propenyl (allyl), butenyl, pentenyl, hexenyl, heptenyl, and the like. The term "$C_1$ to $C_6$ alkoxy" refers to methoxy, ethoxy, iso-propoxy, N-propoxy, n-butoxy, pentoxy, hexyloxy, and the like.

The term "$C_3$ to $C_6$ cycloalkyloxy" refers to cyclopropyloxy, cyclobutyloxy, cyclopentyloxy and cyclohexyloxy.

The term "substituted benzyloxy" refers to groups such as 3-chlorobenzyloxy, 2-methyl-3-chlorobenzyloxy, 2,4-dimethylbenzyloxy, 4-n-propylbenzyloxy, 4-n-butylbenzyloxy, 2-ethyl-4-n-propylbenzyloxy, 2-methoxybenzyloxy, 2,4-dimethoxybenzyloxy, 4-ethoxybenzyloxy, 3-chloro-4-ethoxybenzyloxy, 2-methyl-3chlorobenzyloxy, 4-ethoxybenzyloxy, 4-t-butylbenzyloxy, 2,4-dichlorobenzyloxy, 2,3,4,-trimethoxybenzyloxy, 2,3,4-trimethylbenzyloxy, 3-propoxybenzyloxy, and the like.

The term "substituted phenyl" refers to a mono- or disubstituted halophenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3-chloro-4-bromophenyl, 2-fluorophenyl, and the like; a mono- or dihydroxyphenyl group such as 4-hydroxyphenyl, 3-hydroxyphenyl, 2,4-dihydroxyphenyl and the like; a mono- or disubstituted lower alkylphenyl group such as 4-methylphenyl, 2,4-dimethylphenyl, 2-methylphenyl, 4-isopropylphenyl, 4-ethylphenyl, 3-n-propylphenyl and the like; a mono- or disubstituted lower alkylphenyl ether for example, 2,6-dimethoxyphenyl, 4-methoxyphenyl, 3-ethoxyphenyl, 4-isopropoxyphenyl, 4-t-butoxyphenyl, 3-ethoxy-4-methoxyphenyl; a mono- or disubstituted trifluoromethylphenyl group such as 4-trifluoromethylphenyl, 3,4-di(trifluoromethyl)phenyl, and the like; a mono-or disubstituted carboxyphenyl group, such as 4-carboxyphenyl, 2-carboxyphenyl, 3-carboxyphenyl, 2,4-dicarboxyphenyl, and the like; a phenyl ring substituted by 1 or 2 carboxymethyl groups, such as 2-carboxymethylphenyl, 3-carboxymethylphenyl, 4-carboxymethylphenyl, 2,3-di(carboxymethyl)phenyl, and the like; a phenyl moiety that is mono or disubstituted by hydroxymethyl, resulting in benzyl alcohol type moieties, 2-(hydroxymethyl)phenyl, 4-(hydroxymethyl)phenyl, 3-(hydroxymethyl)phenyl, 3,4-di(hydroxymethyl)phenyl, and the like; phenyl groups mono or disubstituted by amino methyl groups, resulting in benzylamine type moieties, e.g. 2-(aminomethyl)phenyl, 4-(aminomethyl)phenyl, 2,3-di(aminomethyl)phenyl, and the like. It should be noted that phenyl groups disubstituted with bromine are excluded from the above definition. Also the term "substituted phenyl" also represents disubstituted phenyl groups wherein substituents can be different, for example, 3-methyl-4-hydroxyphenyl, 3-chloro-4-hydroxyphenyl, 2-methoxy-4-bromophenyl, 4-ethyl-2-hydroxyphenyl, 2-hydroxy-4-chlorophenyl, 3-trifluoromethyl-4-hydroxyphenyl, 2-carboxy-4-ethoxyphenyl, 2-aminomethyl-4-hydroxymethylphenyl, 4-carboxymethyl-2-methylphenyl, 3-hydroxymethyl-4-chlorophenyl, and like disubstituted phenyl groups bearing different substituents.

Illustrative of the acyl groups

when R₁ is a group of the formula R'—(O)$_m$—CH₂—, m is O and R' is 1,4-cyclohexadienyl, phenyl or substituted phenyl as defined above, are 2-cyclohexa-1,4-dien-1-yl)acetyl, phenylacetyl, 2-(4-chlorophenyl)acetyl, 2-(3-hydroxyphenyl)acetyl, 2-(4-hydroxy-3-methylphenyl)acetyl, 2-(4-hydroxyphenyl)acetyl, 2-(4-bromophenyl)acetyl, 2-(4-ethoxyphenyl)acetyl, 2-(3,4-dimethoxyphenyl)acetyl, and the like; and when m is 1, representative acyl groups are phenoxyacetyl, 2-(3-hydroxyphenoxy)acetyl, 2-(4-hydroxyphenoxy)acetyl, 2-(4chlorophenoxy)acetyl, 2-(3,4-dichlorophenoxy)acetyl, 2-(2-chlorophenoxy)acetyl, 2-(4-methoxyphenoxy)acetyl, 2-(2-ethoxyphenoxy)acetyl, 2-(3,4-dimethylphenoxy)acetyl, 2-(4-isopropylphenoxy)acetyl, 2-(4-methyl-2-carboxyphenoxy)acetyl, 2-(4-aminomethylphenoxy)acetyl, 2-(4-carboxyphenoxy)acetyl, 2-(4-carboxymethylphenoxy)acetyl, 2-(3-trifluoromethylphenoxy)acetyl, 2-(hydroxymethylphenoxy)acetyl, 2-(aminophenoxy)acetyl, and like acyl groups.

Illustrative of the acyl groups

wherein R₁ is a substituted arylalkyl group of the formula

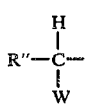

wherein R" is the same as R' defined above or 2-thienyl or 3-thienyl, are the hydroxy substituted arylalkyl groups such as the 2-hydroxy-2-phenylacetyl group of the formula

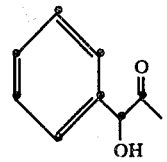

and similar groups wherein the phenyl ring is substituted, for example, 2-hydroxy-2-(4-methoxyphenyl)acetyl, 2-hydroxy-2-(3-chloro-4-hydroxyphenyl)acetyl, 2-hydroxy-2-(4-hydroxyphenyl)acetyl, 2-hydroxy-2-(3-bromophenyl) acetyl, 2-hydroxy-2-(3,5-dichloro-4-hydroxyphenyl)acetyl, 2-hydroxy-2-(3-chloro-4-methoxyphenyl)acetyl, 2-hydroxy-2-(3-chlorophenyl)acetyl, and like groups; the 2-carboxy-2-phenylacetyl group or 2-(protected carboxy)phenylacetyl group of the formula

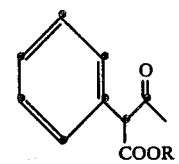

and similar groups wherein the phenyl ring is substituted, for example, 2-protected carboxy-2-phenylacetyl, 2-tert-butoxycarbonyl-2-phenylacetyl, 2-benzyloxycarbonyl-2-(4-chlorophenyl) acetyl, 2-carboxy-2-(4-hydroxyphenyl)acetyl, and like groups; and the 2-amino-2-phenylacetyl or 2-(protected amino)-2-phenylacetyl group of the formula

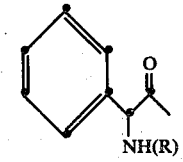

similar groups wherein the phenyl ring is substituted, for example, 2-amino-2phenylacetyl, 2-amino-2-(1,4-cyclohexadien-1-yl)acetyl, 2-amino-2-(4-hydroxyphenyl)acetyl, 2-amino-2-(thien-2-yl)acetyl, 2-(t-butoxycarbonylamino)-2-phenylacetyl and like acyl groups.

Representative of the acyl group

when R₁ is a heteroarylmethyl group of the formula

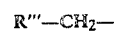

wherein R''' is 2-thienyl, 3-thienylacetyl, 2-furylacetyl, 3-furylacetyl, a 2-thiazolylacetyl group of the formula

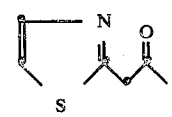

a 2-(1-tetrazolyl)acetyl group of the formula

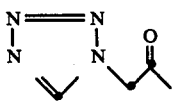

or a 2-(5-tetrazolyl)acetyl group of the formula

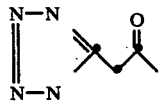

The carboxy and amino groups present in the starting materials of the process for preparing the compounds of this invention are optionally protected; however, the 4-carboxylic acid group of the starting material must be in a soluble salt form for the process for preparing the compounds of this invention. It may be convenient to protect other carboxy or amino groups in the starting material before the process for preparing the compounds of this invention is carried out, since in the subsequent steps required to convert the product compounds to the ultimate products, the 1-oxa β-lactam antibiotics, protection of one or more of such groups is required. Suitable amino and carboxy protecting groups for the compounds of this invention will be discussed below.

Examples of the 7-(S)-acylamino-3-hydroxymethyl-3-cephem-4carboxylic acid sulfone compounds of this invention include:
Benzyl 7-(S)-[2-(fur-2-yl)acetamido]-3-hydroxymethyl-3-cephem-4-carboxylate sulfone,
Phenacyl 7-(S)-[2-(tetrazol-1-yl)acetamido]-3-hydroxymethyl-3-cephem-4-carboxylate sulfone,
Dimethyallyl 7-(S)-[2-amino-2-(4-hydroxyphenyl)acetamido]-3-hydroxymethyl-3-cephem-4-carboxylate sulfone,
p-Chlorophenylacyl 7-(S)-[2-hydroxy-2-(3-chlorophenyl)acetamido]-3-hydroxymethyl-3-cephem-4-carboxylate sulfone,
Dimethylallyl 7-(S)-[2-hydroxy-2-(4-hydroxyphenyl)acetamido]-3-hydroxymethyl-3-cephem-4-carboxylate sulfone,
Phenacyl 7-(S)-(2-amino-2-phenylacetamido)-3-hydroxymethyl-3-cephem-4-carboxylate sulfone,
Benzyl 7-(S)-[2-amino-2-(4-hydroxyphenyl)acetamido]-3-hydroxymethyl-3-cephem-4-carboxylate sulfone,
Dimethylallyl 7-(S)-(2-aminomethylphenyl)acetamido-3-hydroxymethyl-3-cephem-4-carboxylate sulfone,
Sodium 7-(S)-[2-(fur-2-yl)acetamido]-3-hydroxymethyl-3-cephem-4-carboxylate sulfone,
Potassium 7-(S)-[2-(tetrazol-1-yl)acetamido]-3-hydroxymethyl-3-cephem-4-carboxylate sulfone,
Sodium 7-(S)-[2-amino-2-(4-hydroxyphenyl)acetamido]-3-hydroxymethyl-3-cephem-4-carboxylate sulfone,
Lithium 7-(S)-[2-hydroxy-2-(3-chlorophenyl)acetamido]-3-hydroxymethyl-3-cephem-4-carboxylate sulfone,
Potassium 7-(S)-[2-hydroxy-2-(4-hydroxyphenyl)acetamido]-3-hydroxymethyl-3-cephem-4-carboxylate sulfone,
Lithium 7-(S)-(2-amino-2-phenylacetamido)-3-hydroxymethyl-3-cephem-4-carboxylate sulfone,
Sodium 7-(S)-[2-amino-2-(4-hydroxyphenyl)acetamido]-3-hydroxymethyl-3-cephem-4-carboxylate sulfone,
Potassium 7-(S)-(2-aminomethylphenyl)acetamido-3-hydroxymethyl-3-cephem-4-carboxylate sulfone,
7-(S)-[2-(fur-2-yl)acetamido]-3-hydroxymethyl-3-cephem-4-carboxylic acid sulfone,
7-(S)-[2-(tetrazol-1-yl)acetamido]-3-hydroxymethyl-3-cephem-4-carboxylic acid sulfone,
7-(S)-[2-amino-2-(4-hydroxyphenyl)acetamido]-3-hydroxymethyl-3-cephem-4-carboxylic acid,
7-(S)-[2-hydroxy-2-(3-chlorophenyl)acetamido]-3-hydroxymethyl-3-cephem-4-carboxylic acid sulfone,
7-(S)-[2-hydroxy-2-(4-hydroxyphenyl)acetamido]-3-hydroxymethyl-3-cephem-4-carboxylic acid sulfone,
7-(S)-(2-amino-2-phenylacetamido)-3-hydroxymethyl-3-cephem-4-carboxylic acid sulfone,
7-(S)-[2-amino-2-(4-hydroxyphenyl)acetamido]3-hydroxymethyl-3-cephem-4-carboxylic acid sulfone,
7-(S)-(2-aminomethylphenyl)acetamido-3-hydroxymethyl-3-cephem-4-carboxylic acid sulfone.

The preferred 7-(S)-acylamino-3-hydroxymethyl-3-cephem-4-carboxylic acid sulfones of this invention include:
Potassium 7-(S)-benzamido-3-hydroxymethyl-3-cephem-4-carboxlate sulfone,
Potassium 7-(S)-(p-toluylamido)-3-hydroxymethyl-3-cephem-4-carboxylate sulfone,
Potassium 7-(S)-phenoxyacetamido-3-hydroxymethyl-3-cephem-4-carboxylate sulfone,
Potassium 7-(S)-phenylacetamido-3-hydroxymethyl-3-cephem-4-carboxylate sulfone,
Potassium 7-(S)-[2-(thien-2-yl)acetamido]-3-hydroxymethyl-3-cephem-4-carboxylate sulfone,
Potassium 7-(S)-benzyloxycarbamido-3-hydroxymethyl-3-cephem-4-carboxylate sulfone,
Potassium 7-(S)-[D-(5-(2,4-dichlorobenzyloxy-carbonylamino))-5-(benzhydryl carboxylate)-valeramido]-3-hydroxymethyl-3-cephem-4-carboxylate sulfone,
4-Methoxybenzyl 7-(S)-[D-(5-(2,4-dichlorobenzyloxycarbonylamino))-5-((4-methoxybenzyl)carboxylate)valeramido]-3-hydroxymethyl-3-cephem-4-carboxylate sulfone,
Benzhydryl 7-(S)-[D-(5-benzyloxycarbonylamino)-5-(benzhydryl carboxylate)valeramido]-3-hydroxymethyl-3-cephem-4-carboxylate sulfone,
4-Methoxybenzyl 7-(S)-[D-(5-(4-methoxybenzyloxycarbonylamino))-5-((4-methoxybenzyl)carboxylate)valeramido]-3-hydroxymethyl-3-cephem-4-carboxylate sulfone,
Benzhydryl 7-(S)-[D-(5-(2,4-dichlorobenzyloxycarbonylamino))-5-((t-butyl)carboxylate)valeramido]-3-hydroxymethyl-3-cephem-4-carboxylate sulfone,
t-Butyl 7-(S)-[D-(5-(4-methoxybenzyloxycarbonylamino))-5-((t-butyl)carboxylate)valeramido]-3-hydroxymethyl-3-cephem-4-carboxylate sulfone,
t-Butyl 7-(S)-(p-toluylamido)-3-hydroxymethyl-3-cephem-4-carboxylate sulfone,
4-Methoxybenzyl 7-(S)-(p-toluylamido)-3-hydroxymethyl-3-cephem-4-carboxylate sulfone,
t-Butyl 7-(S)-phenoxyacetamido-3-hydroxymethyl-3-cephem-4-carboxylate sulfone,
4-Methoxybenzyl 7-(S)-phenoxyacetamido-3-hydroxymethyl-3-cephem-4-carboxylate sulfone, 4-Methoxybenzyl 7-(S)-phenylacetamido-3-hydroxymethyl-3-cephem-4-carboxylate sulfone, 7-(S)-Benzamido-3-hydroxymethyl-3-cephem-4-carboxylic acid sulfone, 7-(S)-(p-toluylamido)-3-hydroxymethyl-3-cephem-4-carboxylic acid sulfone, 7-(S)-Phenoxyacetamido-3-hydroxymethyl-3-cephem-4-carboxylic acid sulfone, 7-(S)-Phenylacetamido-3-hydroxymethyl-3-cephem-4-carboxylic acid sulfone, 7-(S)-[2-(thien-2-yl)acetamido]-3-hydroxymethyl-3-cephem-4-carboxylic acid sulfone, 7-(S)-Benzyloxycarbamido-3-hydroxymethyl-3-cephem-4-carboxylic acid sulfone, and 7-(S)-[D-(5-(2,4-dichlorobenzyloxycarbonylamino))-5-(benzhydryl carboxylate)valeramido]-3-hydroxymethyl-3-cephem-4-carboxylic acid sulfone.

The more preferred 7-(S)-acylamino-3-hydroxymethyl-3-cephem-4-carboxylic acid sulfone compounds of this invention include:

Benzhydryl 7-(S)-benzamido-3-hydroxymethyl-3-cephem-4-carboxylate sulfone,

Benzhydryl 7-(S)-(p-toluylamido)-3-hydroxymethyl-3-cephem-4-carboxylate sulfone, Benzhydryl 7-(S)-phenoxyacetamido-3-hydroxymethyl-3-cephem-4-carboxylate sulfone, Benzhydryl 7-(S)-phenylacetamido-3-hydroxymethyl-3-cephem-4-carboxylate sulfone, Benzhydryl 7-(S)-[2-(thien-2-yl)acetamido]-3-hydroxymethyl-3-cephem-4-carboxylate sulfone, Benzhydryl 7-(S)-benzyloxycarbamido-3-hydroxymethyl-3-cephem-4-carboxylate sulfone, Benzhydryl 7-(S)-[D-(5-(2,4-dichlorobenzyloxycarbonylamino))-5-(benzhydryl carboxylate)valeramido]-3-hydroxymethyl-3-cephem-4-carboxylate sulfone, Sodium 7-(S)-benzamido-3-hydroxymethyl-3-cephem-4-carboxylate sulfone, Sodium 7-(S)-(p-toluylamido)-3-hydroxymethyl-3-cephem-4-carboxylate sulfone, Sodium 7-(S)-phenoxyacetamido-3-hydroxymethyl-3-cephem-4-carboxylate sulfone, Sodium 7-(S)-phenylacetamido-3-hydroxymethyl-3-cephem-4-carboxylate sulfone, Sodium 7-(S)-[2-(thien-2-yl)acetamido]-3-hydroxymethyl-3-cephem-4-carboxylate sulfone, Sodium 7-(S)-benzyloxycarbamido-3-hydroxymethyl-3-cephem-4-carboxylate sulfone, Sodium 7-(S)-[D-(5-(2,4-dichlorobenzyloxycarbonylamino))-5-(benzhydryl carboxylate)valeramido]-3-hydroxymethyl-3-cephem-4-carboxylate sulfone, Sodium 7-(S)-[D-(5-(2,4-dichlorobenzyloxycarbonylamino))-5-(sodium carboxylate)valeramido]-3-hydroxymethyl-3-cephem-4-carboxylate sulfone.

In general, the process for preparing the 7-(S)-acylamino-3-hydroxymethyl-3-cephem sulfones (formula 1) involves deacetylating a 3-acetoxymethyl compound (formula 2) with citrus acetylesterase immobilized on a functionalized silica gel. The process is carried out by contacting an aqueous solution of the 3-acetoxymethyl compound buffered at a pH of between about 6 and about 8 with citrus acetylesterase immobilized on the functionalized silica gel.

The term "functionalized silica gel" as used herein refers to an aminosilanized silica gel functionalized with an alkane dialdehyde. The acetylesterase enzyme is covalently bonded to the functionalized silica and thus is insolubilized or immobilized thereon and accessible to the buffered solution of the acetoxymethyl compound.

In carrying out the process, the buffered solution of the 3-acetoxymethyl compound can be passed through a column packed with the immobilized enzyme, or alternatively, the immobilized enzyme and the buffered solution can be mixed in a suitable vessel such as a tank or glass flask. Preferably, the solution is passed through a column loaded with the immobilized acetylesterase enzyme.

As stated above, the starting materials for the instant process are dissolved in an aqueous solution of buffer. The amount of starting material dissolved in the aqueous buffer solution is limited only by the solubility of the starting material. The usual range of concentration of the starting material is between about 1 to about 3% w/v. The typical value in this range is 2%, a value obtained with 7-(S)-(2 phenoxyacetamido)-3-acetoxymethyl-3-cephem-4-carboxylic acid sulfone.

The buffering agents used in the instant process are not critical so long as they are used in such a concentration as to keep the aqueous solution containing the starting materials and/or products at a pH between about 6 and about 8. Buffers that can be used are those known in art, e.g., sodium citrate, sodium phosphate, a combination of potassium dihydrogen phosphate and disodium hydrogen phosphate, tris(hydroxymethyl)aminomethane, 4-morpholinepropane sulfonic acid (MOPS), piperazine-N,N'-bis(2-ethane sulfonic acid) (PIPES), N-tris(hydroxymethyl)methyl-2-aminoethane-sulfonic acid (TES), N-2-hydroxyethyl piperazine-N'-2-ethane sulfonic acid (HEPES), and the like. General methods for employing the potassium dihydrogen phosphate/disodium hydrogen phosphate buffer and the tris(hydroxymethyl)aminomethane buffers are found on pages D-186 and D-187 of the *Handbook of Chemistry and Physics*, 59th edition, CRC Press, West Palm Beach, Fla., 33409.

General procedures for using the MOPS, PIPES, TES, and the HEPES buffering agents are found in N. E. Good et al., *Biochemistry*, 5, 1966, page 467.

It will be appreciated that as the concentration of the starting material is increased in the aqueous buffered solution, it is necessary to increase the amount of buffering agent used in order to neutralize the increased amount of acetic acid that is produced in the instant deacetylation procedure. The preferred buffering agents for this procedure are the sodium citrate and sodium phosphate buffers, e.g., 0.2N sodium citrate, 0.3M sodium phosphate, and a mixture of 0.05M sodium citrate and 0.075M sodium phosphate, and 0.2M sodium phosphate.

As stated above, it is necessary to use a sufficient amount of buffering agent in the aqueous solution containing the starting material for the instant process to maintain a pH between about 6 to about 8. The preferred pH range is between about 6 to about 6.5.

The citrus acetylesterase enzyme is known in the art. Specifically, the characteristics and suggested isolation procedure for the enzyme are found in *Methods in Enzymology*, 43, p. 728, 1975, Academic Press, N.Y. The procedure for isolating the enzyme in the instant process is derived from the procedure described in the above reference.

Suggested particle size for the silica gel used as a support for the immobilized enzyme in the instant process is between about 0.06 mm to about 0.20 mm although this is not a critical parameter.

The method for immobilizing the citrus acetylesterase enzyme in the instant process involves:

(1) Derivatizing the silica gel with an amino organosilane. Suitable amino organosilanes include for example, aryl amino and alkyl aminosilanes such as aminophenyltriethoxysilane, and 3-aminopropyltriethoxysilane. The preferred amino organo silane is 3-aminopropyltriethoxysilane (also called triethoxysil-1-yl-3-amino-propane).

(2) Activating the derivatized support. The above aminosilanized silica gel is reacted with an alkane dialdehyde crosslinking agent in order to facilitate bonding to the enzyme. Alkane dialdehyde cross-linking agents which can be reacted with a derivatized silica gel include $C_2$ to $C_{10}$ alkane dialdehydes such as glyoxal, malonaldehyde, succinaldehyde, glutaraldehyde, adipaldehyde, pimelicdialdehyde and subericdialdehyde. The preferred alkane dialdehyde crosslinking agent used to activate the derivatized support is glutaraldehyde.

(3) Immobilizing the enzyme. The citrus acetylesterase is then reacted with the above activated derivatized support.

The flow rate of starting material-containing buffered solution through the immobilized enzyme is set so that at least 90% of the starting material, 7-(S)-acylamino-3-acetoxymethyl-3-cephem-4-carboxylic acid sulfone, is converted to the corresponding 3-hydroxymethyl compound. The appropriate flow rate is determined by percolating a small amount of the buffered solution through a column packed with immobilized enzyme and monitoring the conversion by high performance liquid chromatography. The flow rate is adjusted in order to achieve a conversion of 90% or greater. Once the flow rate has been determined the reaction is periodically monitored by high performance liquid chromatography in order to maintain the appropriate flow rate necessary to achieve the highest percent conversion. Periodic monitoring is preferred because the citrus acetylesterase activity will gradually decrease over a period of time, thus necessitating a decrease in the flow rate in order to increase the residence (contact) time of the starting material on the column. Typical flow rates include 30 ml/hr to 400 ml/hour.

The process is carried out at a temperature of between about 0° C. to about 30° C. The preferred temperature is ambient room temperatures.

The product 7-(S)-acylamino-3-hydroxymethyl-3-cephem-4-carboxylic acid sulfone is isolated from the effluent stream of the immobilized esterase reactor by acidifying the effluent from the column with e.g. 1N hydrochloric acid, and then extracting the free carboxylic acid product into an organic solvent such as ethyl acetate. The deacylated sulfone may also be recovered as the carboxylic acid salt by adding sodium 2-ethylhexanoate to the combined ethyl acetate extracts or alternatively changing solvents from ethyl acetate to methanol and then adding sodium acetate.

The general procedure for the preparation of the citrus acetylesterase enzyme, its immobilization, and the use of the immobilized acetylesterase to deacetylate 7-(S)-acylamino-3-acetoxymethyl-3-cephem-4-carboxylic acid sulfones is as follows:

(1) Silica gel derivatization

Silica gel (E. Merck and Co., Fractosil 200, 70–230 mesh, 62–200μ particle size) is cleaned by deaerating under vacuum a slurry in aqueous 10% nitric acid, heating the slurry for 3 hours at 80° C., then rinsing with water. This clean silica gel is slurried in 5–10 v/w 10% 3-aminopropyltriethoxysilane, then deaerated by vacuum. The pH of the slurry is adjusted to 3–4 with dilute hydrochloric acid, and the slurry is then agitated occasionally during 3 hours of heating at approximately 80° C. The derivatized silica gel is collected on a suction filter, washed with 1 volume of water, and then is dried for about 16 hours at 105° C.

(2) Support Activation

The aminosilanized silica is slurried in 5–10 v/w of a 3% aqueous glutaraldehyde, buffered at pH 7 with a phosphate buffering agent. The slurry is agitated occasionally during a 3 hour period. The resultant activated derivatized silica gel is then washed with water and citrate buffer at a pH of 7.

(3) Enzyme immobilization

A neutral aqueous solution of citrus acetylesterase enzyme is added to the activated derivatized silica gel and this mixture is allowed to interact for between about 4 to about 20 hours. The immobilized enzyme is transferred to a glass or metal column and is washed by percolation of sodium citrate buffer at pH 7 through the packed bed. A solution of the 3-acetoxymethyl-3-cephem cephalosporin sulfone acid in sodium citrate buffer at pH 7 (1–3% concentration) is percolated through the immobilized enzyme. The effluent from the column is monitored by high pressure liquid chromatography, and the flow rate is adjusted to allow a residence time sufficient to provide a 90+% deacetylation of the 3-acetoxymethyl sulfone.

Examples of starting materials that can be used for the instant process include:

7-(S)-[2-(fur-2-yl)acetamido]-3-acetoxymethyl-3-cephem-4-carboxylic acid sulfone, 7-(S)-[2-(tetrazol-1-yl)acetamido]-3-acetoxymethyl-3-cephem-4-carboxylic acid sulfone, 7-(S)-[2-amino-2-(4-hydroxyphenyl)acetamido]-3-acetoxymethyl-3-cephem-4-carboxylic acid sulfone, 7-(S)-[2-hydroxy-2-(3-chlorophenyl)acetamido]-3-acetoxymethyl-3-cephem-4-carboxylic acid sulfone, 7-(S)-[2-hydroxy-2-(4-hydroxyphenyl)acetamido]-3-acetoxymethyl-3-cephem-4-carboxylic acid sulfone, 7-(S)-(2-amino-2-phenylacetamido)-3-acetoxymethyl-3-cephem-4-carboxylic acid sulfone, 7-(S)-[2-amino-2-(4-hydroxyphenyl)acetamido]-3-acetoxymethyl-3-cephem-4-carboxylic acid sulfone, 7-(S)-(2-aminomethylphenyl)acetamido-3-acetoxymethyl-3-cephem-4-carboxylic acid sulfone, Sodium 7-(S)-[2-(fur-2-yl)acetamido]-3acetoxymethyl-3-cephem-4-carboxylate sulfone, Potassium 7-(S)-[2-(tetrazol-1-yl)acetamido]-3-acetoxymethyl-3-cephem-4-carboxylate sulfone, Lithium 7-(S)-[2-amino-2-(4-hydroxyphenyl)acetamido]-3-acetoxymethyl-3-cephem-4-carboxylate sulfone, Sodium 7-(S)-[2-hydroxymethyl-2-(3-chlorophenyl)acetamido]-3-acetoxymethyl-3-cephem-4-carboxylate sulfone, Potassium 7-(S)-[2-hydroxy-2-(4-hydroxyphenyl)acetamido]-3-acetoxymethyl-3-cephem-4-carboxylate sulfone, Lithium 7-(S)-(2-amino-2-phenylacetamido)-3-acetoxymethyl-3-cephem-4-carboxylate sulfone,
Sodium 7-(S)-[2-amino-2-(4-hydroxyphenyl)acetamido]-3-acetoxymethyl-3-cephem-4-carboxylate sulfone,
Potassium 7-(S)-(2-aminomethylphenyl)acetamido-3-acetoxymethyl-3-cephem-4-carboxylate sulfone.

Preferred starting materials for the instant process include:

Potassium 7-(S)-benzamido-3-acetoxymethyl-3-cephem-4-carboxylate sulfone,
Potassium 7-(S)-(para-toluylamido)-3-acetoxymethyl-3-cephem-4-carboxylate sulfone,
Potassium 7-(S)-phenoxyacetamido-3-acetoxymethyl-3-cephem-4-carboxylate sulfone,
Potassium 7-(S)-phenylacetamido-3-hydroxymethyl-3-cephem-4-carboxylate sulfone,
Potassium 7-(S)-[2-(thien-2-yl)acetamido]-3-hydroxymethyl-3-cephem-4-carboxylate sulfone,
Potassium 7-(S)-benzyloxycarbamido-3-hydroxymethyl-3-cephem-4-carboxylate sulfone,
Potassium 7-(S)-[D-(5-(2,4-dichlorobenzyloxycarbonylamino))-5-(benzhydryl carboxylate)valeramido]-3-acetoxymethyl-3-cephem-4-carboxylate sulfone,
Sodium 7-(S)-[D-(5-(2,4-dichlorobenzyloxycarbonylamino))-5-((4-methoxybenzyl)carboxylate)valeramido]-3-acetoxymethyl-3-cephem-4-carboxylate sulfone,
Potassium 7-(S)-[D-(5-(4-methoxybenzyloxycarbonylamino))-5-((4-methoxybenzyl)carboxylate)valeramido]-3-acetoxymethyl-3-cephem-4-carboxylate sulfone,
Sodium 7-(S)-[D-(5-(2,4-dichlorobenzyloxycarbonylamino))-5-((t-butyl)carboxylate)valeramido]-3-acetoxymethyl-3-cephem-4-carboxylate sulfone,
Potassium 7-(S)-[D-(5-(4-methoxybenzyloxycarbonylamino))-5-((t-butyl)carboxylate)valeramido]-3-acetoxymethyl-3-cephem-4-carboxylate sulfone,
7-(S)-[D-(5-(2,4-dichlorobenzyloxycarbonylamino))-5-((4-methoxybenzyl)carboxylate)valeramido]-3-acetoxymethyl-3-cephem-4-carboxylic acid sulfone,
7-(S)-[D-(5-(4-methoxybenzyloxycarbonylamino))-5-((4-methoxybenzyl)carboxylate)valeramido]-3-acetoxymethyl-3-cephem-4-carboxylic acid sulfone,
7-(S)-[D-(5-(2,4-dichlorobenzyloxycarbonylamino))-5-((t-butyl)carboxylate)valeramido]-3-acetoxymethyl-3-cephem-4-carboxylic acid sulfone,
7-(S)-[D-(5-(4-methoxybenzyloxycarbonylamino))-5-((t-butyl)carboxylate)valeramido]-3-acetoxymethyl-3-cephem-4-carboxylic acid sulfone.

More preferred substrates for the instant process include:

7-(S)-Benzamido-3-acetoxymethyl-3-cephem-4-carboxylic acid sulfone,
7-(S)-(p-toluylamido)-3-acetoxymethyl-3-cephem-4-carboxylic acid sulfone,
7-(S)-Phenoxyacetamido-3-acetoxymethyl-3-cephem-4-carboxylic acid sulfone,
7-(S)-Phenylacetamido-3-acetoxymethyl-3-cephem-4-carboxylic acid sulfone,
7-(S)-[2-(thien-2-yl)acetamido]-3-acetoxymethyl-3-cephem-4-carboxylic acid sulfone,
7-(S)-Benzyloxycarbamido-3-acetoxymethyl-3-cephem-4-carboxylic acid sulfone,
7-(S)-[D-(5-(2,4-dichlorobenzyloxycarbonylamino))-5-(benzyhydryl carboxylate)valeramido]-3-acetoxymethyl-3-cephem-4-carboxylic acid sulfone,
Sodium 7-(S)-benzamido-3-acetoxymethyl-3-cephem-4-carboxylate sulfone,
Sodium 7-(S)-(p-toluylamido)-3-acetoxymethyl-3-cephem-4-carboxylate sulfone,
Sodium 7-(S)-phenoxyacetamido-3-acetoxymethyl-3-cephem-4-carboxylic acid sulfone,
Sodium 7-(S)-phenylacetamido-3-hydroxymethyl-3-cephem-4-carboxylate sulfone,
Sodium 7-(S)-[2-(thien-2-yl)acetamido]-3-acetoxymethyl-3-cephem-4-carboxylate sulfone,
Sodium 7-(S)-benzyloxycarbamido-3-acetoxymethyl-3-cephem-4-carboxylate sulfone,
Sodium 7-(S)-[D-(5-(2,4-dichlorobenzyloxycarbonylamino))-5-(sodium carboxylate)valeramido]-3-acetoxymethyl-3-cephem-4-carboxylate sulfone,
Sodium 7-(S)-[D-(5-(2,4-dichlorobenzyloxycarbonylamino))-5-(benzhydryl carboxylate)valeramido]-3-acetoxymethyl-3-cephem-4-carboxylate sulfone.

The starting materials employed in the process for making the compounds of this invention are obtained by oxidizing a 7-(R)-acylamino-3-acetoxymethyl-3-cephem-4-carboxylic acid to the corresponding sulfone. The 7-(R)-acylamino-3-acetoxymethyl-3-cephem-4-carboxylic acid sulfone is then epimerized to the corresponding 7-(S)-acylamino compound.

The above sequence of reactions is illustrated by the following reaction scheme:

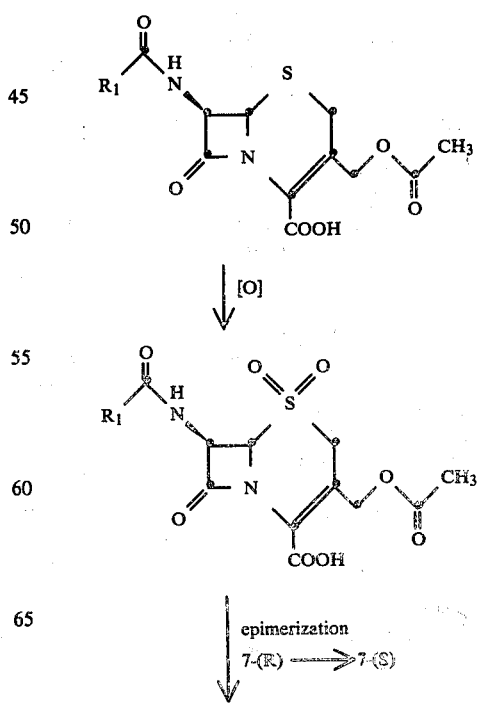

-continued

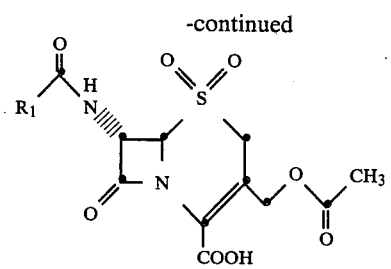

In the above formulas R₁ is as defined for formula 1.

The preparation of the 7-(R)-acylamino-3-acetoxymethyl-3-cephem-4-carboxylic acid sulfone is best carried out in an aqueous reaction medium maintained at a pH between about 5.0 and about 6.0 with an excess of potassium hydrogen persulfate. The oxidation proceeds well at temperatures of about 15° to about 45°. The sulfone is recovered from the aqueous reaction medium by acidifying the mixture to form the free sulfone carboxylic acid and extraction of the latter with a suitable water immiscible solvent such as ethyl acetate.

The epimerization of the 7-(R)-acylamino-3-acetoxymethyl-3-cephem-4-carboxylic acid sulfone is preferably carried out in an aqueous medium as follows. A slurry of the sulfone free acid in water is treated with an aqueous solution of sodium acetate containing at least an equimolar amount of sodium acetate. An aqueous solution of piperazine is then added dropwise until the pH of the solution is about 9.5 to 10. With the pH adjusted, the epimerization mixture is stirred for about 5 to 15 minutes and the product recovered as follows. Ethyl acetate is added to the mixture which is then acidified to a pH of about 2.0 with concentrated hydrochloric acid. The 7-(S)-acylamino-3-acetoxymethyl-3-cephem-4-carboxylic acid sulfone is then extracted with ethyl acetate.

The preparation of the cephalosporin sulfones and the epimerization to these 7-(S)-acylamino sulfones are described in co-pending application Ser. Nos. 442,079 and 442,077 filed this even date.

The 7-(S)-acylamino-3-hydroxymethyl 4-carboxylic acid sulfone compounds of this invention as discussed above are intermediates in the synthesis of 1-oxa β-lactam antibiotics.

The first step of this synthesis of 1-oxa β-lactam involves electrolytic reduction of the 3-hydroxymethyl sulfone compounds of this invention to 2-(R)-sulfinic acid-3-(S)-acylamino azetidinones, represented by formula 3

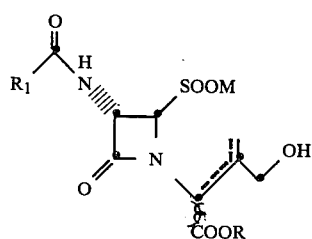

wherein R₁ is as described for formula 1, M is a lithium, potassium, sodium, ammonium or a substituted ammonium cation, and R is hydrogen, a carboxylic acid protecting group, lithium, potassium, sodium, ammonium or substituted ammonium cation. The sulfinic acid azetidinones of formula 3 are prepared as described in co-pending application Ser. No. 442,075, filed this even date. As described therein, the 7-(S)-acylamino-3-hydroxymethyl-4-carboxylate sulfone compounds of the instant invention are reduced at the cathode of an electrolysis cell usually comprised of a mercury pool cathode, a platinum anode, and a cationic resin separating the cathode and anode compartments. A suitable electrolyte can be sodium perchlorate, lithium perchlorate or sodium acetate. The anolyte is preferably a phosphate buffer at pH 2.7.

The reduction is carried out preferably at a temperature between about −10° C. and about 10° C. and at a reduction potential between about −1.0 V and about −1.9 V vs. a standard calomel electrode.

The 3-hydroxymethyl sulfone ester is dissolved in methyl alcohol containing a proton source such as an organic acid, e.g. acetic acid. The electrolyte of choice, e.g. sodium acetate, is then added to the solution to achieve a 0.1M concentration of the electrolyte.

The solution is then placed in the cathode compartment and the electrolysis apparatus is flushed with argon until any oxygen present is removed. The electrolysis can be carried out at constant potential or at constant current. The progress of the electrolysis can be followed by use of analytical HPLC on an aliquot of the reduction mixture.

Following the electrolysis the reduction product mixture is extracted in the cold with a water immiscible organic solvent, preferably ethyl acetate.

The above electrolysis procedure to produce the sulfinic acid azetidinones of formula 3 produces 2 isomers of this general class of sulfinic acids, i.e. the β,γ azetidinone sulfinic acid compounds represented by formula 4

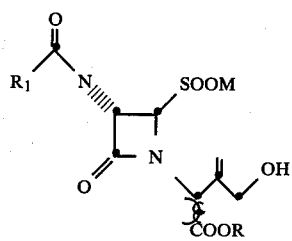

or the α,β azetidinone sulfinic acid compounds represented by formula 5

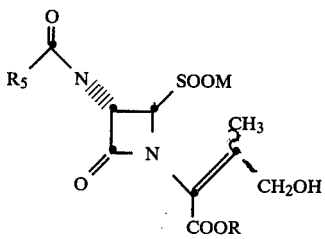

The carboxy groups of the 7-(S)-acylamino-3-hydroxymethyl-3-cephem sulfones (formula 1) should be protected during the electrolysis when an organic solvent or an organic solvent plus water is used.

Accordingly, the choice of carboxy protecting groups should be limited to ones that are stable to the electrolysis process (i.e., not easily reduced), thus ruling out protecting groups such as p-nitrobenzyl, 2,2,2-trichloroethyl, 2,2,2-tribromoethyl, 2,2-di-bromoethyl, 2-iodoethyl, 2,2-diiodoethyl, 2,2,2-tri-iodomethyl, and like protecting groups having nitro, activated halogeno or cyano substituents. In addition, the carboxy protecting groups used must not be so acid-labile as to be removed by the proton source used in the electrolysis, i.e. the carboxylic acid having a pKa between about 0 to about 5. Acid-labile protecting groups that should be avoided are the silyl groups such as trimethylsilyl. If these limitations are heeded, protecting groups that can be used on either the starting materials of formula 1 or the products of formulas 4 and 5 of the electrolysis process where the term "protected carboxy" is specified are those commonly used carboxylic acid protecting groups such as tert-butyl, benzyl, diphenylmethyl(-benzhydryl), 4-methoxybenzyl, $C_2$–$C_6$ alkanoyloxymethyl, phenacyl, chlorophenacyl, dimethylallyl, and the like. Preferred carboxylic acid protecting groups are benzhydryl, 4-methoxybenzyl and tert-butyl.

It is not essential that amino groups present in the 3-hydroxymethyl-3-cephem sulfones be protected in the electrolysis process. However, if unprotected, it is necessary to take their presence into account when calculating the amount of proton source needed in the electrolytic reduction to an azetidinone sulfinic acid (formula 3), as the unprotected amino groups will consume some of the proton concentration needed for the electrolysis reduction. If an amino-protecting group is used, it is again necessary, as with carboxylic acid protecting groups, to avoid the use of easily reducible groups, e.g. the 4-nitrobenzoxycarbonyl group, the 2,2,2-trichloroethoxycarbonyl, the β-haloethyloxycarbonyls, etc. With these precautions observed, the protecting groups that can be used in situations where "protected amino" groups are specified are those known in the cephalosporin art, such as the benzyloxycarbonyl group, the 2,4-dichlorobenzyloxycarbonyl group, and the 4-methoxybenzyloxycarbonyl group.

In the foregoing definitions, amino and carboxy protecting groups are not exhaustively defined. Many such protecting groups are well known in the art and the use of other groups equally applicable to the compound of this invention, such as those described in Theodora W. Greene, "Protective Groups In Organic Synthesis", John Wiley and Sons, 1981, N.Y. will be recognized as suitable. Thus, there is no novelty or inventiveness asserted with regard to the "protecting groups" in this specification.

The β,γ-azetidinone sulfinic acid compounds produced by the electrolysis procedure are converted to a β,γ epi-oxazoline compound of the formula 6

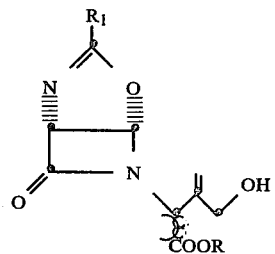

The conversion to the β,γ epi-oxazolines is carried out by reacting the azetidinone sulfinic acid compounds with an oxidizing agent. The reaction generally is carried out by mixing at least one molar equivalent and up to about 1.5 molar equivalents of the oxidizing agent with each molar equivalent of the β,γ-azetidinone sulfinic acid compound. Preferably, the ratio of reactants is from about 1.0 to about 1.1 molar equivalents of oxidizing agent per molar equivalent of the azetidinone sulfinic acid compound. Preferably, the reaction is carried out in a suitable inert organic solvent at a temperature from about 0° C. to about 30° C., for a period sufficient for the completion of the reaction. This oxidation reaction can be carried out on an azetidinone sulfinic acid compound that has been isolated and/or purified, or the oxidizing agent can be added directly to the catholyte of the preceding electrolysis after it has been removed from the cathode compartment.

The term "inert organic solvent" means an organic solvent which, under the conditions of the epi-oxazoline formation, does not appreciably react either with the reactants or with the products. Suitable inert organic solvents include, for example, aromatic hydrocarbons, such as benzene, toluene, ethylbenzene, cumene, and the like; halogenated hydrocarbons, such as carbon tetrachloride, chlorobenzene, bromoform, bromobenzene, methylene chloride, ethylene chloride, 1,1,2-trichloroethane, ethylene dibromide, and the like; amides, such as N,N-dimethylformamide, and the like; alcohols, such as methanol, ethanol, and the like; esters, such as ethyl acetate, and the like; nitriles, such as acetonitrile, and the like; and the other appropriate inert solvents. Preferred solvents include N,N-dimethylformamide, acetonitrile, ethylacetate, methylene chloride, and the like.

The oxidizing agent used in this reaction can be any of a wide range of such agents. Typical agents include, for example, lead (IV) compounds such as lead tetraacetate, lead oxide, and the like; manganese (IV) compounds, such as manganese acetoacetonate, manganese oxide, and the like; sodium hypochlorite; N-haloimides, such as N-bromosuccinimide, and the like; ammonium cerium nitrate; and other like oxidizing compounds. Preferably, the oxidizing agent is a lead (IV) compound, in particular, lead tetraacetate, or an N-bromoimide, in particular, N-bromosuccinimide.

The temperature of the oxidation reaction generally is from about 0° C. to about 30° C. Preferably, the reaction temperature is at the lower end of this range, generally from about 0° C. to about 5° C.

Typically the oxidation reaction is complete in a very short time, generally a matter of a few minutes on small scale reactions. Normally the time of the reaction will be no longer than about 1 hour.

The above oxidation reaction is more fully described and claimed in U.S. application Ser. No. 442,052, filed this even date.

The β,γ-epi-oxazoline compounds discussed above are converted to the 1-oxa β-lactam compounds as described in U.S. Pat. Nos. 4,220,766, 4,271,295 and 4,271,296 herein incorporated by reference.

The β,γazetidinone sulfinic acid compounds wherein the C-3 substituent is a carbamato side chain, i e., an azetidinone sulfinic acid compound of the formula 7

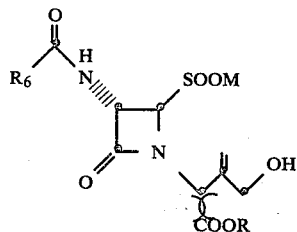

wherein $R_6$ is $C_1$ to $C_6$ alkoxy, $C_3$ to $C_6$ cycloalkyloxy, benzyloxy or substituted benzyloxy as described above are produced by the electrolysis process discussed above. The above $\beta,\gamma$-azetidinone sulfinic acid compounds of formula 7 are converted directly to an isomeric mixture of a cyclization product, i.e., a 3-exomethylene 1-oxa $\beta$-lactam compound of the formula

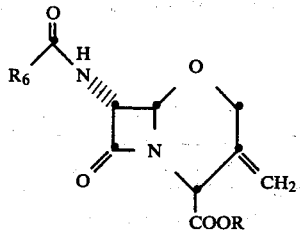

and a 3-methyl 1-oxa $\beta$-lactam compound of the formula

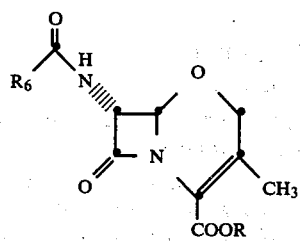

The azetidinone sulfinic acid (formula 7) is reacted in an inert organic solvent with lead tetraacetate in liquid sulfur dioxide in the presence of copper (II) ion at a temperature between about $-25°$ C. and about $0°$ C. Between about 1.0 and about 2.5 molar equivalents of lead tetraacetate per molar equivalent of azetidinone sulfinic are used.

The amount of sulfur dioxide used can be between about 1 to about 3 molar equivalents per molar equivalent of substrate azetidinone compound, preferably in excess of the molar equivalents of substrate compound is used. The sulfur dioxide can be used as a solvent by itself or in addition to an inert organic solvent such as ethyl acetate, methylene chloride, tetrahydrofuran, dioxane, and the like.

A readily available source of copper (II) ion is copper sulfate. Between about 10 to about 15 milligrams of copper sulfate per millimole of azetidinone sulfinic acid compound is a suitable amount.

The 3-exomethylene 1-oxa $\beta$-lactam compound obtained can be easily isomerized to the 3-methyl 1-oxa $\beta$-lactam compound in the presence of a base such as triethylamine. The 3-methyl 1-oxa $\beta$-lactam compounds are intermediates in the synthesis of 1-oxa $\beta$-lactam antibiotic compounds, such as those described in U.S Pat. Nos. 4,226,866 and 4,138,486.

The cyclization reaction of the 3-carbamato azetidinone sulfinic acid compound (formula 7) to the 1-oxa $\beta$-lactam intermediates is described in co-pending U.S. application, Ser. No. 442,080, filed this even date. The conversion of the 1-oxa $\beta$-lactam intermediate produced in this cyclization process to the 1-oxa $\beta$-lactam antibiotic compounds is described in the above co-pending U.S. application and U.S. Pat. Nos. 4,226,866 and 4,138,486, said patents here incorporated by reference.

The $\alpha,\beta$-azetidinone sulfinic acid compounds of the above formula 5 provided by the electrolysis of a formula 1 compound encompass both the 2'-Z isomer, represented by the partial formula

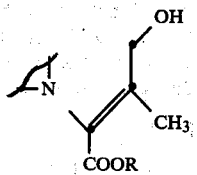

and the 2'-E isomer, represented by the partial formula

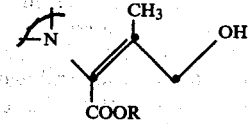

In the formula 5, $R_5$ is 1,4 cyclohexadienyl, phenyl or substituted phenyl as described for a compound of formula 1.

The above $\alpha,\beta$ sulfinic acids (formula 5) are minor products in the electrolytic process for making the $\beta,\gamma$ sulfinic acid compounds. The isomerization of the double bond from the $\beta,\gamma$ positions to the $\alpha,\beta$ position is caused by basic species in the catholyte and/or the work-up procedure. In this regard, the cathode salt used is especially effective in catalyzing the isomerization of the double bond, and in particular the tri-n-butylammonium para-toluylsulfonate salt has been found to give the largest amount of the $\alpha,\beta$ sulfinic acid isomer. A specific set of reaction conditions for the electrolysis process that will produce the $\alpha,\beta$ sulfinic acid isomer exclusively involves the use of methanol as the liquid medium, acetic acid as the proton source, tri-n-butylammonium para-toluylsulfonate as the catholyte salt with the temperature of the reaction between about $-10°$ C. to about $10°$ C.

The $\alpha,\beta$ azetidine sulfinic acids discussed above are converted to the corresponding $\alpha,\beta$-unsaturated epi-oxazoline of the formula

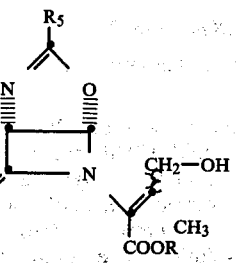

prepared by the same process used for the $\beta,\gamma$ sulfinic acid compounds. In the above formula for the $\alpha,\beta$ epi-oxazoline compounds $R_5$ is the same as for the corresponding $\alpha,\beta$ sulfinic acids, as discussed above. These $\alpha,\beta$ epi-oxazoline compounds are then converted to 1-oxa $\beta$-lactam antibiotic compounds using the same processes as for the $\beta,\gamma$ epi-oxazoline compounds, as discussed above.

The following examples and preparations are supplied to further illustrate the instant invention, and are not meant to limit the scope of the invention. As used in the following examples, the abbreviations "IMER", "n.m.r." and "F.A.B.M.S." stand for immobilized enzyme reactor, nuclear magnetic resonance and fast atom bombardment mass spectrum, respectively. Unless otherwise noted, all n.m.r. spectra were taken in DMSO-d$_6$ at 90 MHZ. DMSO, assigned a value of δ2.49, is used as the reference in the n.m.r. spectra, unless otherwise noted. All temperatures are in degrees centigrade.

PREPARATION 1

Preparation of porous silica gel carrier a. Amino-silanization.

Silica gel (FRACTOSIL ® 200 particle size 120–230 mesh, 63–125 mμ, mean pore diameter 9 nm, E. Merck Co., P.O. Box 2000, Rahway, N.J. 07065, 100 g) was cleaned by addition to 10% nitric acid (100 ml). The slurry was evaporated in vacuo, then heated on a steam bath (2 hours) with occasional stirring. The porous silica gel was collected by suction filtration and washed with copious amounts of deionized water. The clean porous silica gel was added to a 10% aqueous solution of triethoxysil-1-yl-3-aminopropane (100 ml, liquid reagent obtained from Aldrich Chemical Company) and the pH of the resultant mixture was adjusted to about 3.5 to about 4.0 by the addition of 4N hydrochloric acid. The mixture was heated on a steam bath (approximately 2 hours) with occasional stirring. The amino-silanized porous silica gel was collected by suction filtration, washed with deionized water (250 ml), then dried in an oven (110°) overnight.

b. Condensation of amino-silylized porous silica gel with glutaraldehyde (1) Amino-silanated FRACTOSIL ® 200 (25 g, from a. above) was added to a mixture of 8% aqueous glutaraldehyde solution (100 ml) and 0.3M pH 7 phosphate buffer (150 ml). The mixture was dearated under vacuum, and then swirled occasionally over a 3 hour period. The condensed amino-silanated porous silica gel carrier was collected by suction filtration and washed with copious amounts of 0.3M pH 7 phosphate buffer.

(2) The above procedure (b. 1) is carried out, substituting 0.2M sodium citrate buffer (pH 7, 300 ml) for the phosphate buffer, doubling the amount of glutaraldehyde solution used, and using more amino-silanated FRACTOSIL ® 200 (80 g vs. 25 g) than is used in b. 1.

PREPARATION 2

Preparation of the immobilized enzyme reactor (IMER)

a. Enzyme preparation

Fresh orange peel (2000 g) was blended in 500 g batches with 2 volumes of cold 0.25M sodium chloride solution for 1.5 minutes each in a large Waring blender. The resultant slurry was stirred in a chillroom for 1 hour, while maintaining the pH between 7.0 to 7.5 with 10% sodium hydroxide solution. The resultant solids were filtered on four layers of cheesecloth by suction filtration, and the filtrate was lyophilized to yield 250 g of solids. A portion of these lyophilized solids (192 g) was suspended in cold water (960 ml, total volume), then stirred for 10 minutes. The insoluble material was removed from this solution by centrifugation and filtration through filter paper. Decolorizing charcoal (3% w/v) was added to the filtrate and stirred for 10 minutes. The charcoal was then removed from the filtrate by centrifugation and filtration through packed glass wool. To the resultant filtrate (1200 ml) was added ammonium sulfate (197 g), and the solution was stirred for 1 hour. The insoluble material was removed by centrifugation and discarded. To the cold centrifugate solution was added an additional portion of ammonium sulfate (235 g) to provide 60% saturation, and this solution was stirred for 2 hours and the resultant solids were separated by centrifugation. The solids were dissolved in 0.002M potassium hydrogen phosphate buffer (150 ml), then dialyzed overnight against buffer (5 L). The solution was then centrifuged to remove a slight precipitate which formed, yielding 236 ml of the enzyme preparation.

b. Column preparation

The enzyme solution from a. above was added to the activated porous amino-silanized silica gel from Preparation 1 b. 1. The mixture was swirled occasionally at room temperature for about 2 hours, then refrigerated. The porous silica gel, now containing the immobilized acetyl-estearase, was packed into a 60 ml cylindrical dropping funnel and the column was washed with 0.3M phosphate buffer (pH 7), then 0.1M sodium citrate buffer (pH 7.0).

EXAMPLE 1

Sodium 7-(S)-benzamido-3-hydroxymethyl-3-cephem-4-carboxylate sulfone 7-(S)-Benzamido-3-acetoxymethyl-3-cephem-4-carboxylic acid sulfone (13.2 g) was dissolved in 0.2M aqueous sodium citrate solution (38.9 g sodium citrate in 630 ml water). The pH of this solution was adjusted to 7.0 by the addition of 1.0 N sodium hydroxide solution (approximately 30 ml). The solution was then percolated through the IMER (40–50 ml/h). The effluent (680 ml) collected from the IMER was layered with ethyl acetate (800 ml), chilled to 0° C. in an ice-alcohol bath, then the pH was adjusted to 2.5 by the addition of 1 N hydrochloric acid. The layers were separated and the aqueous layer was extracted with ethyl acetate (400 ml, 2×). The ethyl acetate extracts and the ethyl acetate layer were combined. Ice was added to the combined ethyl acetate solution which was then washed with an acidified saturated aqueous sodium chloride solution (250 ml, 2×). The solution was dried over magnesium sulfate and filtered. Sodium acetate (2.8 g) was added to the filtrate and the solution was stirred at room temperature for 3 h. and refrigerated overnight. The cream-colored crystals which deposited were collected by suction filtration, then washed with cold ethyl acetate. The crystals were allowed to air-dry first and then were dried in vacuo to yield 8.6 g of sodium 7-(S)-benzamido-3-hydroxymethyl-3-cephem-4-carboxylate: F.A.B.M.S. (m+1)=389.

EXAMPLE 2

Benzhydryl 7-(S)-benzamido-3-hydroxymethyl-3-cephem-4-carboxylate sulfone

The IMER from Example 1 was washed with 0.2 M aqueous sodium citrate solution (approx. 250 ml). Additional eluant and IMER washings containing the equivalent of 14 g of starting material were layered with ethyl acetate (1 L), then chilled to 0° C. in an ice-alcohol bath. Diphenyldiazomethane (5.0 g) was added to the stirred, chilled solution, and the pH of the resultant solution was adjusted to 2.4 by the addition of 1 N hydrochloric acid. After 3 h, the phases were separated, and the aqueous layer was extracted with ethyl acetate (400 ml, 2×). The ethyl acetate extracts and the ethyl acetate layer were then combined. The ethyl acetate solution was washed with 0.3 M phosphate solution (pH 7, 400 ml, 2×) and with saturated aqueous sodium chloride (1×), dried over magnesium sulfate, filtered, and the solvent removed in vacuo to yield the benzhydryl ester as 11.4 g of a yellow foam. The foam was triturated with diethyl ether (approx. 75 ml) resulting in the formation of a gum. The mother liquor was decanted and the gum was dissolved in ethyl acetate (400 ml). The ethyl acetate solution was then washed sequentially with acidified saturated sodium chloride (250 ml, 2×), 0.3 M phosphate solution (250 ml, 2×, pH 7) and saturated sodium chloride solution (1×). The ethyl acetate solution was then dried over magnesium sulfate, filtered, and the solvent was removed to yield 10 g of benzhydryl 7-(S)-benzamido-3-hydroxymethyl-3-cephem-4-carboxylate sulfone: n.m.r. δ 4.08 (s, 2, 3'-CH$_2$), 4.26 (dd, 2, C$_2$-H), 5.23 (dd, 1, C$_7$-H), 5.62 (d, 1, C$_6$-H), 6.94 (s, 1, benzhydryl methine), proton 7.2–8.0 (m, 15, aromatic protons), 9.54 (d, 1, amido proton).

EXAMPLE 3

Benzhydryl 7-(S)-(p-toluylamido)-3-hydroxy-methyl-3-cephem-4-carboxylate sulfone A 1% solution of 7-(S)-(p-toluylamido)-3-acetoxymethyl-3-cephem-4-carboxylic acid in 0.3 M phosphate buffer (pH 6.8) was percolated through the IMER prepared as described above. The effluent from the IMER column (400 ml) was layered with ethyl acetate (700 ml) and chilled to −1° C. in an alcohol-ice bath. Diphenyldiazomethane (1.3 g) was added to the chilled solution and the pH of the solution was adjusted to 2.5 by the addition of 1 N sulfuric acid. The layers were separated after 0.75 h, and the aqueous layer was extracted with ethyl acetate (75 ml) and the extract was combined with the organic layer. After approximately 1.5 hours, the organic layer was red-orange. The organic layer was washed further with aqueous phosphate solution (pH 7.0, 2×), and with saturated aqueous sodium chloride solution (1×), dried over magnesium sulfate, filtered and the solvent removed by evaporation to yield 2.97 g of benzhydryl 7-(S)-(p-toluylamido)-3-hydroxymethyl-3-cephem-4-carboxylate sulfone: n.m.r. (100 MHz) δ 2.47 (s, 3, methyl of toluylamido), 4.11 (d, 2, C$_3$'-H), 4.29 (ABq, 2, C$_2$-H), 5.26 (dd, 1 C$_7$-H), 5.64 (d, 1, C$_6$-H), 6.96 (s, 1, benzhydryl methine), 7.2 to 7.8 (m, 14, aromatic protons) 9.48 (d, 1, amido proton).

EXAMPLE 4

Sodium 7-(S)-(2-phenoxyacetamido)-3-hydroxymethyl-3-cephem-4-carboxylate sulfone 7-(S)-(2-Phenoxyacetamido)-3-acetoxymethyl-3-cephem-4-carboxylic acid sulfone was dissolved in a 0.2 M sodium citrate solution (pH approx. 7.2, adjusted with 1 N sodium hydroxide) until the solution was approximately 2% in the sulfone starting material. The sulfone solution was filtered and percolated through the IMER (200 ml/h, later at 100 ml/h) until a total of 90 g of the sulfone had been treated on the IMER.

IMER effluent (1000 ml) was layered with ethyl acetate (1000 ml) and this mixture was chilled to 0° C. in an ice-alcohol bath. The pH of the chilled solution was adjusted to 2.5 by the addition of 1 N hydrochloric acid with vigorous stirring. Ice was added to the mixture to keep it chilled, the layers were separated and the aqueous layer was extracted with ethyl acetate (600 ml). The ethyl acetate extract was combined with the organic layer, and the solution was washed with acidified aqueous saturated sodium chloride solution (300 ml, 2×). The solution was dried over magnesium sulfate, filtered, and the filtrate was divided into two 735 ml portions.

To one 735 ml portion, sodium acetate (1.9 g) was added with stirring, and the resultant solution was allowed to stir for an additional 3 h at room temperature. The precipitate was collected by suction filtration and then washed with ethyl acetate. The resultant white crystals were air-dried to yield 6.7 g of product, which, when dried in vacuo for 7 h, gave 6.1 g of sodium 7-(S)-(2-phenoxyacetamido)-3-hydroxymethyl-3-cephem-4-carboxylate sulfone: n.m.r. δ 3.94 (2xq, 4 total, C-2 and C-3' protons), 4.59 (s, 2, phenoxyacetamido methylene), 5.10 (d, 1, $J^{C\text{-}7H}=2$ Hz, C-6 proton), 5.3 (dd, 1, $J^{C\text{-}6H}=2$Hz, $J^{amide}=8.3$ Hz, C-7 proton), 6.8–7.4 (m, 5, aromatic), 9.4 (d, 1, $J^{C\text{-}7H}=8.3$ Hz, amido proton).

EXAMPLE 5

Benzhydryl 7-(S)-(2-phenoxyacetamido)-3hydroxymethyl-3-cephem-4-carboxylate sulfone Effluent (1500 ml) from the IMER of Example 4 was layered with ethyl acetate (1000 ml) and diphenyldiazomethane (12.0 g) was added to the mixture. The mixture was chilled to 0° C. in an ice-alcohol bath, and the pH of the mixture was adjusted with stirring to 2.5 by the addition of 1 N hydrochloric acid. After 0.33 h additional diphenyldiazomethane (1.2 g) was added to the solution. After 2 h the layers were separated, and the aqueous layer was extracted with ethyl acetate (400 ml, 2×). The ethyl acetate extracts were combined with the ethyl acetate layer, and the resultant ethyl acetate solution was washed with 0.3 M phosphate solution (2×, pH 7.0), then with aqueous saturated sodium chloride solution (400 ml, 2×). The ethyl acetate solution was then dried over magnesium sulfate, filtered and the solvent was removed in vacuo to give a syrup-like mass. A total of 1000 ml of methylene chloride was added to the syrup, then removed in vacuo to yield 31.8 g of the benzhydryl ester yellow foam.

Part of the yellow foam (2.0 g) was triturated with diethyl ether (200 ml), the triturate was filtered, and the filtrate evaporated to approximately ⅓ of its original volume. The cream-colored solid which precipitated was collected by suction filtration and washed with ether, to yield 0.5 g of non-crystalline benzhydryl 7-(S)-(2-phenoxyacetamido)-3-hydroxymethyl-3-cephem-4-carboxylate sulfone: n.m.r. δ 4.07 (d, 2, C$_3$'-H), 4.26 (ABq, 2, C$_2$-H), 4.68 (s, 2, acetamido CH$_2$), 5.22 (dd, 1, C$_7$-H), 5.26 (t, 1, hydroxy proton) 5.57 (d, 1, C$_6$-H), 6.96 (s, 1, benzhydryl methine), 7.2 to 7.6 (m, 15, aromatic protons), 9.22 (d, 1, amide proton).

EXAMPLE 6

Benzhydryl 7-(S)-(2-phenylacetamido)-3-hydroxymethyl-3-cephem-4-carboxylate sulfone 7-(S)-(2-Phenylacetamido)-3-acetoxymethyl-3-cephem-4-carboxylic acid (15 g) was dissolved in a buffer solution (0.05 M sodium citrate plus 0.075 M sodium phosphate, pH 7.0, 1500 ml) while maintaining the pH of the solution between pH 7.0–7.2 by the addition of 1

N sodium hydroxide. The solution was then percolated through the IMER (at 60 to 100 ml/h).

The collected effluent (1250 ml) was layered with ethyl acetate (600 ml) and the resultant emulsion was chilled to 0° C. in an ice-alcohol bath. Diphenyldiazomethane (5.0 g) was added to the stirred emulsion, and the mixture was stirred for an additional 2.5 h, while the pH of the reaction mixture was maintained at about 2.5 by the addition of 1 N hydrochloric acid.

The phases were separated and the aqueous phase was extracted with ethyl acetate (400 ml, 2×). The ethyl acetate extracts and the ethyl acetate phase were combined, washed with 0.3 M sodium phosphate solution (pH 7, 2×) and saturated aqueous sodium bicarbonate solution (300 ml, 1×). The combined ethyl acetate solution was dried over magnesium sulfate, filtered, and the solvent was removed in vacuo to give a yellow foam. The foam was pulverized, yielding 12.6 g of benzhydryl 7-(S)-(2-phenylacetamido)-3-hydroxymethyl-3-cephem-4-carboxylate sulfone: n.m.r. δ 3.60 (s, 2, 2-phenylacetamido CH$_2$), 4.06 (s, 2, C$_3$'-H), 4.22 (ABq, 2, C$_2$-H), 5.10 (dd, 1, C$_7$-H), 5.47 (d, 1, C$_6$-H), 6.90 (s, 1, benzhydryl methine), 7.2 to 7.6 (m, 15, aromatic protons), 9.07 (d, 1, amido proton).

EXAMPLE 7

Sodium 7-(S)-(2-phenylacetamido)-3-hydroxymethyl-3-cephem-4-carboxylate sulfone 7-(S)-(2-Phenylacetamido)-3-acetoxymethyl-3-cephem-4-carboxylic acid (13.0 g) was dissolved in buffer (0.05 M sodium citrate plus 0.075 M sodium phosphate, pH 7.0, 1300 ml) while maintaining the pH of the solution between pH 7.0–7.2 by the addition of 1 N sodium hydroxide solution. This solution was percolated through the IMER (60 to 100 ml/h).

The IMER was then washed with buffer. A portion of the collected effluent (1600 ml) was layered with ethyl acetate (1000 ml), and the emulsion was cooled to 0° in an ice-alcohol bath. The layers were separated, and the aqueous layer was extracted with ethyl acetate (300 ml, 2×). The ethyl acetate extracts and the ethyl acetate layer were combined, washed with acidified saturated sodium chloride solution (2×), dried over magnesium sulfate, and filtered. Sodium acetate (3.0 g) was added to the vigorously stirred filtrate, and the mixture was stirred for an additional 4 h. The precipitate was collected by suction filtration, then dried in vacuo to give 9.75 g (78% yield) of sodium 7-(S)-(2-phenylacetamido)-3-hydroxymethyl-3-cephem-4-carboxylate sulfone: F.A.B.M.S. (m+1)=403.

EXAMPLE 8

Sodium 7-(S)-[2-(thien-2-yl)acetamido]-3-hydroxymethyl-3-cephem-4-carboxylate sulfone Sodium 7-(S)-[2-(thien-2-yl)acetamido]-3-acetoxymethyl-3-cephem-4-carboxylate sulfone was dissolved in 0.3 M pH 7 phosphate buffer to yield a 2% w/v solution which was then percolated through the IMER at 300 to 400 ml/hr.

A portion of the effluent from the above IMER procedure was chilled to 0° in an ice-alcohol bath, layered with ethyl acetate, and the pH of the emulsion adjusted to 2.5 by the addition of 1 N hydrochloric acid. Immediately thereafter, the layers were separated, and the aqueous layer was extracted with ethyl acetate. The ethyl acetate extract and the ethyl acetate layer were combined, washed with aqueous saturated sodium chloride solution, dried over magnesium sulfate, filtered and the filtrate was evaporated to dryness in vacuo. The residue was dissolved in methanol (1000 ml), and then a methanol solution of sodium acetate (110% of the equivalents required for neutralization of the 4-carboxylic acid) was added. The precipitate was collected by filtration, washed with methanol and dried to yield 6.3 g of sodium 7-(S)-[2-(thien-2-yl)acetamido]-3-hydroxymethyl-3-cephem-4-carboxylate sulfone.

EXAMPLE 9

Benzhydryl 7-(S)-[2-(thien-2-yl)acetamido]-3-hydroxymethyl-3-cephem-4-carboxylate sulfone To part of the effluent (1000 ml) from the IMER of Example 8 above was added ethyl acetate (500 ml) and the emulsion which formed was chilled to 0°. Diphenyldiazomethane (7.8 g) was added to the cold emulsion and the pH was lowered to 2.5 by the addition of 1 N hydrochloric acid. After stirring for 1.5 h. the layers were separated, the aqueous layer extracted with ethyl acetate and the extract combined with the ethyl acetate layer. The ethyl acetate solution was washed with acidified saturated aqueous sodium chloride solution, dried over magnesium sulfate and filtered. To the filtrate were added a few seed crystals of the ester and the solution was refrigerated for 4 days. The crystals were collected by suction filtration, washed with cold ethyl acetate, then dried in vacuo to yield 13.2 g of cream-white crystals of benzhydryl 7-(S)-[2-(thien-2-yl)acetamido]-3-hydroxymethyl-3-cephem-4-carboxylate sulfone: n.m.r. (Reference: tetramethylsilane) δ 3.85 (s, 2, 2-(thien-2-yl) acetamido methylene protons), 4.02 (s, 2, C$_3$'-H), 4.23 (q, 2, C$_2$-H), 5.11 (dd, 1, C$_7$-H), 5.26 (t, 1, hydroxy proton) 5.50 (d, 1, C$_6$-H), 6.9 to 7.6 (m, 13, aromatic protons), 6.96 (s, 1, benzhydryl methine proton), 9.12 (d, 1, amido proton).

EXAMPLE 10

Benzhydryl 7-(S)-benzyloxycarbamido-3-hydroxymethyl-3-cephem-4-carboxylate sulfone a. IMER preparation—A citrus acetylesterase IMER was prepared as above using Fractosil 200 (23.7 g), 8% glutaraldehyde (100 ml) and citrus acetylesterase (31 ml). 2.5 h was allowed for esterase binding. After packing the immobilized enzyme into the column, the column was washed with buffer.

b. Deacylation—Sodium-7-(S)-benzyloxycarbamido-3-acetoxymethyl-3-cephem-4-carboxylate sulfone (17.45 g) was dissolved in 0.2 M phosphate solution (pH 7.0, 873 ml) to yield a 2% solution of sulfone, and the pH of this solution was adjusted from 6.6 to 6.9 with 1 N sodium hydroxide solution. The solution was then percolated through the column (40 to 50 ml/h) a total of 3 times, followed by adding citrus acetylesterase (10 ml) directly to the eluant. As the reaction mixture was percolating through the IMER, it was necessary to periodically remove by filtration the precipitate that formed in the solution on standing before it was percolated through the IMER.

Part of the eluant (610 ml) from the IMER was chilled to approximately 3° C. in an ice-alcohol bath and an ethyl acetate solution (200 ml) of diphenyldiazomethane (3.25 g) was added. The pH of the emulsion was adjusted to 2.6 with 1 N sulfuric acid. After the mixture was stirred for 2 h. the layers were allowed to separate. The ethyl acetate layer was washed with a 1:1 pH 7.0 buffer/sodium chloride solution (150 ml, 4×), dried over magnesium sulfate, filtered, and the solvent was evaporated in vacuo to give an orange-colored foam. The foam was dried (in vacuo) for 0.75 h. Chloroform (20 ml) was added to the orange foam followed by the addition of diethyl ether to facilitate precipitation of the product while stirring. Additional chloroform (5 ml) was added to dissolve the gum that formed and sonication of this solution gave white crystals which were collected by filtration. Spectral analysis confirmed that the crystals (5.45 g, 58%) were benzhydryl 7-(S)-benzyloxycarbamido-3-hydroxymethyl-3-cephem-4-carboxylate sulfone: n.m.r. (100 MHz) δ 4.09 (d, 2, $C_3'$-H), 4.25 (ABq, 2, $C_2$-H), 5.04 (dd, 1, $C_7$-H), 5.26 (t, 1, hydroxy proton) 5.47 (d, 1, $C_6$-H), 6.93 (s, 1, benzhydryl methine), 7.2 to 7.6 (m, 15, aromatic protons), 8.52 (d, 1, amido proton); analysis: calculated: C, 61.19: H, 4.59; N, 5.10; S, 5.83; found: C, 61.78; H, 4.79; N, 5.41; S, 6.27.

EXAMPLE 11

Sodium 7-(S)-[D-(5-(2,4-dichlorobenzoxycarbonylamino))-5-(benzhydryl carboxylate)valeramido]-3-hydroxymethyl-3-cephem-4-carboxylate sulfone A 2% solution of 7-(S)-[D-(5-(2,4-dichlorobenzoxycarbonylamino))-5-(benzhydryl carboxylate)-valeramido]-3-acetoxymethyl-3-cephem-4-carboxylic acid in 0.2 M sodium citrate (pH adjusted to 7.0 with 1 N sodium hydroxide) was percolated through the IMER (50 to 35 ml/h). Part of the eluant from the IMER (500 ml) was chilled in an ice-alcohol bath, and ice was added. Ethyl acetate (500 ml) was added to the cold eluant and the pH of the mixture was adjusted to 2.5 by the addition of 1 N hydrochloric acid. The layers were separated, and the aqueous layer was extracted with ethyl acetate (250 ml, 2×). The ethyl acetate layer and extracts were combined, washed with saturated aqueous sodium chloride solution, dried over magnesium sulfate and filtered. Sodium acetate (3.12 g) was added to the filtrate with stirring and stirring was continued for 4 h at room temperature. The crystals formed were collected by suction filtration, washed with ethyl acetate and air-dried to give 5.7 g of sodium 7-(S)-[D-(5-(2,4-dichlorobenzoxycarbonylamino))-5-(benzhydryl carboxylate)valeramido]-3-hydroxymethyl-3-cephem-4-carboxylate sulfone: F.A.B.M.S. (m+1)=600.

EXAMPLE 12

Benzhydryl 7-(S)-[D-(5-(2,4-dichlorobenzoxycarbonylamino))-5-(benzhydryl carboxylate)valeramido]-3-hydroxymethyl-3-cephem-4-carboxylate sulfone Benzhydryl 7-(S)-[D-(5-(2,4-dichlorobenzoxycarbonylamino))-5-(benzhydryl carboxylate)valeramido]-3-acetoxymethyl-3-cephem-4-carboxylate sulfone (14.7 g) was added to a 0.2 M sodium citrate solution (pH adjusted to 7.0 by the addition of 1 N sodium hydroxide to yield a 1% solution of sulfone), and the solution was percolated through an IMER (50 to 35 ml/h). The eluant was refrigerated and diluted with ethyl acetate. Diphenyldiazomethane (10.0 g) was added to the cold eluant and the pH of the mixture was adjusted to 3.5 by the addition of 1 N hydrochloric acid. After stirring the mixture for 4 h, the layers were separated and the aqueous layer was extracted with ethyl acetate (250 ml, 2×). The ethyl acetate layer and extracts were combined, washed with a saturated sodium chloride solution, then dried over magnesium sulfate and filtered. Diphenyldiazomethane (1.6 g) was added to the filtrate and the solution was stirred overnight. Additional diphenyldiazomethane (1.0 g) was added. The mixture was stirred for approx. 6 h, and was then evaporated to yield 22.3 g of yellow foam. The foam was triturated with diethyl ether, the liquid decanted, the pale yellow solid dissolved in methylene chloride, and the solution evaporated to dryness in vacuo. The trituration procedure was repeated yielding a foam (14.9 g, 78% yield) of benzhydryl 7-(S)-[D-(5-(2,4-dichlorobenzoxycarbonylamino))-5-(benzhydryl carboxylate)valeramido]-3-hydroxymethyl-3-cephem-4-carboxylate sulfone: n.m.r. (DMSO $d_6$) δ 1.40–2.45 (br. m., 6, valeramido methylenes), 4.04 (d, 2, $C_3'$-H), 4.11 (ABq, 2, $C_2$-H), 4.54 (m, 1, valeramido methine), 5.06 (dd, 1, $C_7$-H, J=2.5, 8), 5.21 (t, 1, hydroxy proton), 5.40 (d, 1, $C_6$-H, J=2.5), 6.79 (s, 1, benzhydryl methine on valeramido ester), 6.89 (s, 1, benzhydryl methine on C-4 ester), 7.2 to 7.7 (br. m., 23, aromatic protons), 8.85 (d, 2, S-amido proton), 8.97 (d, 1, C-7 amido proton).

I claim:

1. A compound of the formula

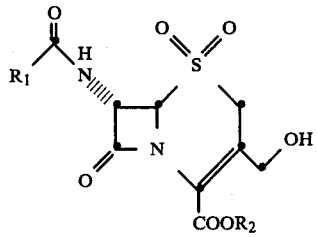

wherein $R_1$ is
  a. $C_1$ to $C_7$ alkyl, $C_3$ to $C_7$ alkenyl, chloromethyl, dichloromethyl, 4-carboxybutyl, 4-formylbutyl, 4-protected carboxybutyl, 4-amino-4-carboxybutyl or 4-protected amino-4-protected carboxybutyl; or
  b. $C_1$ to $C_6$ alkoxy, $C_3$ to $C_6$ cycloalkyloxy, benzyloxy or substituted benzyloxy, wherein the substituents are one to three groups chosen from the group consisting of $C_1$ to $C_4$ alkyl, $C_1$ to $C_4$ alkoxy and chloro; or
  c. 1,4-cyclohexadienyl, phenyl or substituted phenyl wherein the substituents are one or two groups chosen from the group consisting of chlorine, bromine, hydroxy, trifluoromethyl, $C_1$ to $C_4$ alkyl, $C_1$ to $C_4$ alkoxy, carboxy, carboxymethyl, hydroxymethyl, aminomethyl and protected aminomethyl; or
  d. an arylalkyl group of the formula $R'$—(O)$_m$—CH$_2$— wherein R' is 1,4-cyclohexadienyl, phenyl or substituted phenyl as defined above, and m is zero or one; or
  e. a substituted arylalkyl group of the formula

wherein R'' is R' as defined above, 2-thienyl, or 3-thienyl; W is hydroxy or protected hydroxy, carboxy or protected carboxy, amino or protected amino; or f. a heteroarylmethyl group of the formula

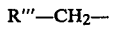

wherein R''' is 2-thienyl, 3-thienyl, 2-furyl, 3-furyl, 2-thiazolyl, 5-tetrazolyl or 1-tetrazolyl; and $R_2$ is hydrogen, a carboxylic acid protecting group, lithium cation, sodium cation or potassium cation.

2. A compound of claim 1, wherein $R_1$ is $C_1$ to $C_7$ alkyl, $C_3$ to $C_7$ alkenyl, chloromethyl, dichloromethyl, 4-carboxybutyl, 4-formylbutyl, 4-protected carboxybutyl, 4-amino-4-carboxybutyl or 4-protected amino-4-protected carboxybutyl.

3. A compound of claim 2, wherein $R_1$ is 4-protected amino-4-protected carboxybut-1-yl.

4. A compound of claim 3, wherein $R_1$ is 4-(2,4-dichlorobenzyloxycarbonylamino)-4-(benzhydryl carboxylate)but-1-yl.

5. A compound of claim 4, wherein $R_2$ is hydrogen.

6. A compound of claim 4, wherein $R_2$ is benzhydryl.

7. A compound of claim 4, wherein $R_2$ is sodium cation.

8. A compound of claim 1, wherein $R_1$ is $C_1$ to $C_6$ alkoxy, $C_3$ to $C_6$ cycloalkyloxy, benzyloxy or substituted benzyloxy, wherein the substituents are one to three groups chosen from the group consisting of $C_1$ to $C_4$ alkyl, $C_1$ to $C_4$ alkoxy and chloro.

9. A compound of claim 8, wherein $R_1$ is benzyloxy.

10. A compound of claim 9, wherein $R_2$ is benzhydryl or sodium cation.

11. A compound of claim 1, wherein $R_1$ is 1,4-cyclohexadienyl, phenyl or substituted phenyl.

12. A compound of claim 11, wherein $R_1$ is phenyl or p-methylphenyl.

13. A compound of claim 12, wherein $R_2$ is benzhydryl or sodium cation.

14. A compound of claim 1, wherein $R_1$ is an arylalkyl group of the formula

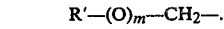

15. A compound of claim 14, wherein R' is phenyl.

16. A compound of claim 15, wherein $R_2$ is benzhydryl or sodium cation.

17. A compound of claim 1, wherein $R_1$ is a heteroarylmethyl group of the formula

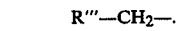

18. A compound of claim 17, wherein R''' is thien-2-yl.

19. A compound of claim 18, wherein $R_2$ is benzhydryl or sodium cation.

* * * * *